US009933347B2

(12) United States Patent
Pieterse

(10) Patent No.: US 9,933,347 B2
(45) Date of Patent: Apr. 3, 2018

(54) METHOD AND SYSTEM FOR DETERMINING FLUID DENSITY

(71) Applicant: Stellenbosch University, Stellenbosch (ZA)

(72) Inventor: Cornelius Louwrens Pieterse, Kenhardt (ZA)

(73) Assignee: Stellenbosch University, Stellenbosch (ZA)

( * ) Notice: Subject to any disclaimer, the term of this patent is extended or adjusted under 35 U.S.C. 154(b) by 0 days.

(21) Appl. No.: 15/511,121

(22) PCT Filed: Sep. 15, 2015

(86) PCT No.: PCT/IB2015/057092
§ 371 (c)(1),
(2) Date: Mar. 14, 2017

(87) PCT Pub. No.: WO2016/042481
PCT Pub. Date: Mar. 24, 2016

(65) Prior Publication Data
US 2017/0276583 A1    Sep. 28, 2017

(30) Foreign Application Priority Data

Sep. 15, 2014   (ZA) .................................. 2014/06733

(51) Int. Cl.
*H01J 49/00*         (2006.01)
*G01N 9/24*          (2006.01)
(Continued)

(52) U.S. Cl.
CPC ............. *G01N 9/24* (2013.01); *G01N 27/002* (2013.01); *B05B 5/0255* (2013.01)

(58) Field of Classification Search
None
See application file for complete search history.

(56) References Cited

U.S. PATENT DOCUMENTS 8,364,229 B2 *   1/2013   Simpson ............ A61B 5/14532
                                                 600/309
9,768,463 B2 *   9/2017   Goeltz .................. H01M 8/188
(Continued)

FOREIGN PATENT DOCUMENTS

WO     2015128844     9/2015
WO     WO 2015128844 A1 *  9/2015   ............. G01N 13/02

OTHER PUBLICATIONS

Stark, John P W et al: "Electrospray pulsation: A diagnostic to understand cone-jet stability and minimum flow" Journal of Applied Physics, American Insitute of Physics, US, vol. 115, No. 4, Jan. 28, 2014, XP012181071, ISSN: 0021-8979, DOI: 10.1063/1.4862805 III. Results; p. 044905, cols. 1,2; figure 2.

(Continued)

*Primary Examiner* — Andrew Smyth
(74) *Attorney, Agent, or Firm* — Andrus Intellectual Property Law, LLP

(57) ABSTRACT

A method and system for determining a density of a fluid is provided. The method is carried out using an electrospraying apparatus connected in the system. At a first step fluid is introduced into an emitter of the electrospraying apparatus. A voltage is applied between the emitter and a counter-electrode spaced apart from the emitter for a number of intermittent time periods, wherein the duration of at least some of the time periods during which the voltage is applied progressively decreases. The current between the emitter and the counter-electrode is measured for each time period during which a voltage is applied and the shortest time period for which a current reading is obtained is recorded. The shortest time period is used to calculate the density of the fluid in the emitter.

15 Claims, 3 Drawing Sheets

(51) Int. Cl.
*G01N 27/00* (2006.01)
*B05B 5/025* (2006.01)

(56) References Cited

U.S. PATENT DOCUMENTS

| | | | | |
|---|---|---|---|---|
| 2008/0177164 A1* | 7/2008 | Heller | ............... | C12Q 1/006 600/347 |
| 2010/0155496 A1* | 6/2010 | Stark | ............... | B05B 5/0255 239/3 |
| 2012/0248306 A1* | 10/2012 | Sakairi | ............ | G01N 33/4972 250/288 |
| 2014/0028260 A1* | 1/2014 | Goeltz | ............... | H01M 8/188 320/127 |

OTHER PUBLICATIONS

Pieterse Cornelius Louwrens: "Comments on: Electrohydrodynamic drop-on-demand patterning in pulsed cone jet mode at various frequencies by Joonghyuk Kim, Hyuncheol Oh and Sang"; Journal of Aerosol Science, Pergamon, Amsterdam, NL, vol. 57, Dec. 11, 2012 pp. 199-202, XP028970607, ISSN: 3021-8502, DOI: 10.1016/J.JAEROSCI.2012.11.0101. Introduction; p. 199, paragraph 2.
Kim, Joonghyuk et al: "Electrohydrodynamic drop-on-demand patterning in pulsed cone-jet mode at various frequencies" Journal of Aerosol Science, vol. 39, May 8, 2008, pp. 819-825.
International Search Report and Written Opinion for International Application No. PCT/IB2015/057092 dated Dec. 4, 2015.

\* cited by examiner

METHOD AND SYSTEM FOR DETERMINING FLUID DENSITY

CROSS-REFERENCE(S) TO RELATED APPLICATIONS

This application claims priority to PCT/IB2015/057092, filed Sep. 15, 2015, and published in English on Mar. 24, 2016 as Publication No. WO 2016/042481A1, which claims priority to South African provisional patent application number 2014/06733 filed on Sep. 15, 2014, which is incorporated by reference herein.

FIELD OF THE INVENTION

This invention relates to a method and system for determining the density of a fluid.

BACKGROUND TO THE INVENTION

Density is a physical property of a fluid and is defined as the mass of fluid per unit volume. Fluid density can be determined by the direct measurement of mass and volume.

Instruments that measure fluid density have wide-ranging applications in the pharmaceutical, petroleum, chemical and food industries, as well as in scientific or engineering research fields.

The density of a fluid, in particular a liquid can be measured using instruments such as a hydrometer, a pycnometer, or a digital density meter, or a densitometer. Methods employing such instruments, generally require a relatively large sample of liquid to be able to determine the density of the liquid with reasonable accuracy.

Few techniques on a micro-scale, i.e. which use an amount of liquid in the microliter range per density determination have been developed.

Moreover, to the applicant's knowledge, a method and system capable of determining both the density and the surface tension of a liquid under the same conditions, does not yet exist.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a method of determining a density of a fluid, the method including the steps of:
  introducing the fluid into an emitter of an electrospraying apparatus;
  applying a voltage between the emitter and a counter-electrode spaced apart from the emitter for a number of intermittent time periods, wherein the duration of at least some of the time periods during which the voltage is applied progressively decreases;
  measuring current between the emitter and the counter-electrode for each time period;
  identifying and recording a shortest time period for which a current reading between the emitter and counter-electrode is obtained; and
  calculating the density of the fluid as a function of the shortest time period.

A further feature of the invention provides for the density of the fluid to be calculated using the function:

$$\rho = \left(\frac{\varepsilon_0}{3}\right)^3 \left(\frac{TE^3}{\pi\gamma}\right)^2,$$

wherein $\rho$ is the fluid density, $\varepsilon_0$ is the vacuum permittivity constant, T is the shortest time period, E is the electric field at an aperture of an emitter tip, and $\gamma$ is the surface tension of the fluid.

Further features of the invention provide for the voltage applied between the emitter and the counter-electrode during time periods to be sufficient to produce an electrospray of the fluid; and for the voltage to be reduced to a voltage that does not produce an electrospray of the fluid, or for the voltage to be switched off, in between the time periods.

Still further features of the invention provide for the time periods during which the voltage is applied to start with an initial time period that is associated with a selected upper density limit so as to allocate sufficient time for electrospraying to occur; for the duration of the time periods during which the voltage is applied to decrease sequentially in a step-wise manner; and for the duration of the time periods during which the voltage is applied to decrease in steps of 1 ms or less.

A yet further feature of the invention provides for the initial time period to be associated with an upper density limit that is more than or equal to 2000 kg/m$^3$.

The invention also provides a system for measuring a density of a fluid comprising an electrospraying apparatus having an emitter through which the fluid is drawn, at least one counter-electrode spaced apart from the emitter, and a voltage source configured to apply a voltage between the emitter and the counter-electrode to create an electrospray of fluid from the emitter, a device for measuring the voltage applied between the emitter and the counter-electrode and a device for measuring the current flowing in the system as a result of electrospray of the fluid between the emitter and the counter-electrode, characterized in that a processing module in communication with at least the voltage source, the voltage measuring device and the current measuring device, is configured to operate the voltage source to apply a voltage between the emitter and the counter electrode for a number of intermittent time periods, wherein the duration of at least some of the time periods is progressively decreased, and wherein the processing module is further configured to read the current measuring device, and to identify and record the shortest time period for which a current reading is obtained in the system.

A further feature of the invention provides for the processing module to be configured to calculate the density of the fluid as a function of the shortest time period.

A further feature of the invention provides for the function to be:

$$\rho = \left(\frac{\varepsilon_0}{3}\right)^3 \left(\frac{TE^3}{\pi\gamma}\right)^2,$$

wherein $\rho$ is the fluid density, $\varepsilon_0$ is the vacuum permittivity constant, T is the shortest time period, E is the electric field at an aperture of an emitter tip and $\gamma$ is the surface tension of the fluid.

Still further features of the invention provide for the voltage source to be a programmable direct current voltage source; for a software application to be resident on the processing module and executable by the processing module to progressively decrease at least some of the time periods for which a voltage is applied; for a software application to be resident on the processing module and executable by the processing module to sequentially decrease the time period for which a predetermined voltage is applied in a step-wise manner, to stop decreasing the time period when a current is no longer detected by the current measuring device; and to reduce the voltage to a voltage that does not produce an electrospray, preferably to switch the voltage off, in between time periods.

A further feature of the invention provides for the electrospray apparatus to be configured to electrospray under atmospheric conditions or, alternatively, for the electrospray apparatus to be configured to electrospray within an isolation medium and for at least the electrospray apparatus and counter-electrode to be located within a hermetically sealed container filled with the isolation medium.

BRIEF DESCRIPTION OF THE DRAWINGS

The invention will now be described, by way of example only, with reference to the accompanying drawings in which.

DETAILED DESCRIPTION WITH REFERENCE TO THE DRAWINGS

An electrospray is an apparatus that employs electricity to produce a fine plume of nano- or micro-sized droplets. Electrosprays are used in many applications such as mass spectrometry, the electrospinning of nanofibres, space-based electrostatic propulsion systems, the deposition of particles for nanostructures, pharmaceutical drug delivery, air purification, and advanced printing techniques, amongst others.

An electrospray apparatus in its most basic form consists of an emitter with a small aperture that channels the fluid, preferably a liquid, to be sprayed through the aperture. Using a voltage source, an electrical potential is applied between the emitter, acting as an electrode, and a counter-electrode spaced away by an appropriate distance from the emitter. The liquid is emitted by development of a strong electrostatic field at the tip of the emitter as a result of the electrical potential. At a particular threshold voltage, the slightly rounded tip of the liquid at the aperture of the emitter inverts and forms what is known as a Taylor cone and emits a jet of liquid. As this jet travels away from the aperture, it eventually becomes unstable and separates into a spray of highly charged droplets.

Figure 1:
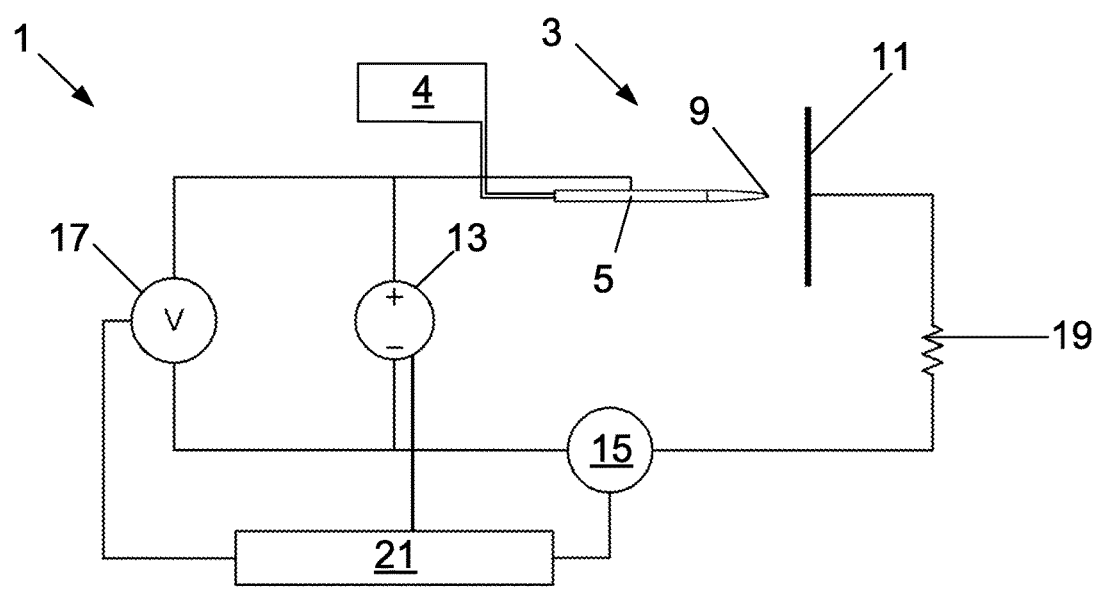
FIG. 1 is a schematic illustration of an embodiment of the system for measuring the density of a fluid according to the invention.

An embodiment of a system (1) for measuring the density of a fluid, preferably a liquid, is illustrated in FIG. 1. The system (1) includes an electrospraying apparatus (3) in fluid communication with a chamber (4) that houses a liquid. A conductive emitter (5), in this embodiment a capillary, extends from the chamber and terminates in a narrow tip (9) which has a small aperture that forms an outlet for the capillary. The tip is selected to be coated with or made from a material selected from gold, platinum, silver and copper or their alloys. A counter-electrode (11) is positioned proximate the tip at a selected distance of approximately ten times that of the radius of the aperture in the tip (9). The separation distance may be varied, depending on the experimental conditions required. The counter-electrode (11) has any suitable shape and size in accordance with the required electric field characteristics, it can, for example, be a plate with a planar surface or a ring electrode.

A direct current voltage source (13), which may be adjustable, is connected across the counter-electrode (11) and the tip (9) of the emitter (5) so as to apply a voltage between them. A current measuring device, in this embodiment an ammeter (15), is connected in series with the counter-electrode (11) and tip (9) to measure the current in the electrospraying system, more particularly that which results from the electrospray of the fluid between the emitter tip and the counter-electrode. A voltage measuring device, in this embodiment a voltmeter (17), is connected in parallel with the voltage source (13). A resistor (19) is connected in series with the electrospray apparatus and acts as a ballast to stabilise the current, decrease the likelihood of undesirable electrical discharges occurring, and to stabilise the electrospray of a fluid.

The electrospraying apparatus is further provided with a processing module (21) in communication with the voltage source (13), voltmeter (17) and ammeter (15). The processing module (21) is configured to read the ammeter, voltmeter and a clock, in this embodiment an internal clock of the processing module (21), and to issue instructions to the voltage source (13). It should be appreciated that in order to do so, the processing module may have storage means, display means and suitable software operating thereon which is capable of issuing instructions to the various components of the system (1) to allow it to perform the appropriate functions.

Figure 2:
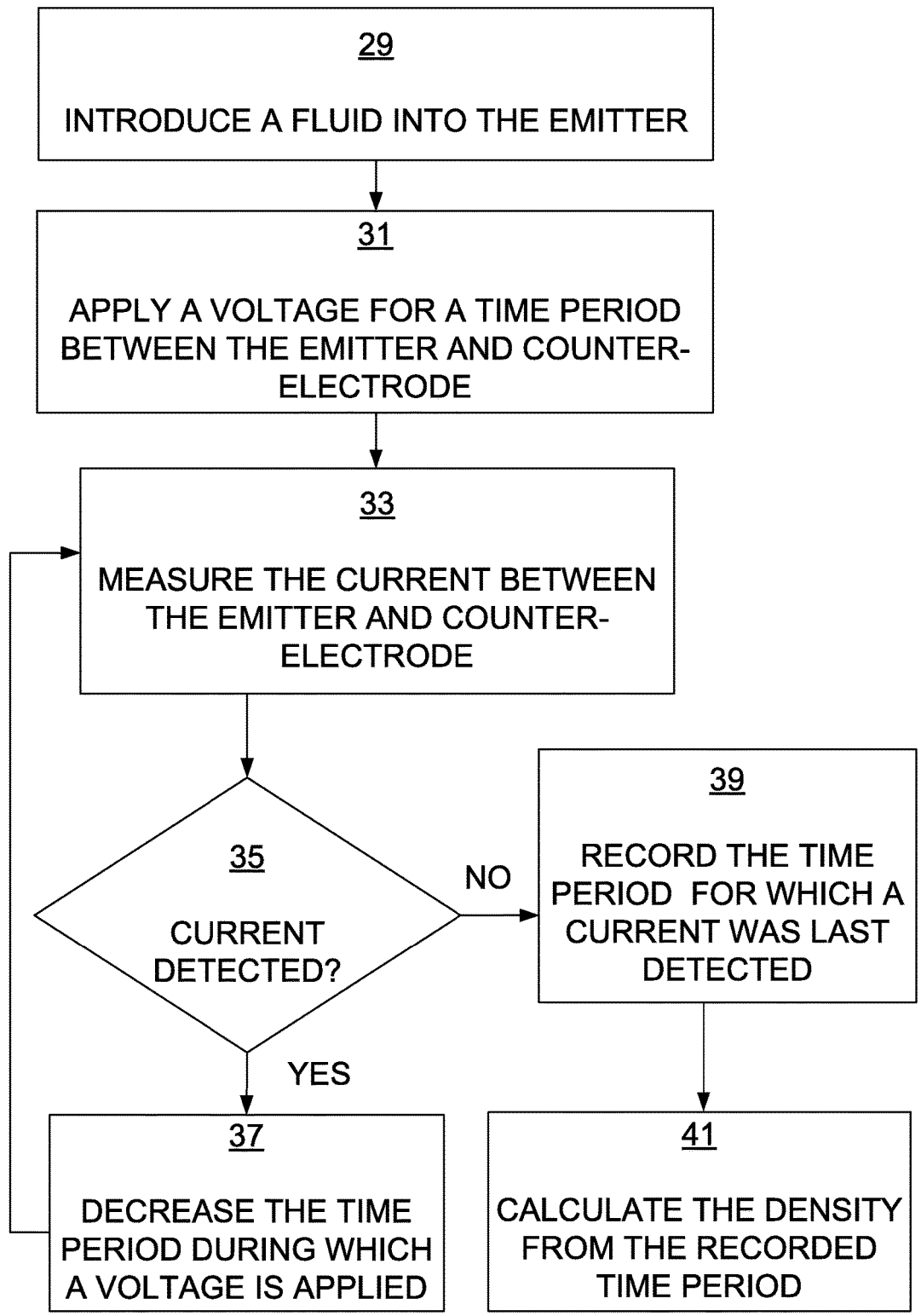
FIG. 2 is a flow diagram that illustrates a method of determining the density of a fluid using the system of FIG. 1.

A method of determining the density of a fluid using the system (1) described above with reference to FIG. 1, will now be described with reference to the flow diagram shown in FIG. 2. Firstly, a fluid is introduced into the emitter of an electrospraying apparatus (29). At a second step (31), a voltage source is used to apply a selected voltage between the emitter and the counter-electrode of the electrospraying apparatus for an initial time period that is associated with a selected upper density limit. An upper density limit of 2000 kg/m$^3$ may be selected which may correspond to a time period that provides sufficient time for electrospraying to occur. The selected voltage is a voltage that produces an electrospray of the fluid from the emitter. The voltage must effect the required electric field at the aperture of the emitter to obtain electrospray of the fluid.

At a next step (33), the current in the system is measured using the ammeter and the processing module continuously reads the ammeter. If current is measured or detected between the emitter and counter-electrode (35), the processing module issues instructions to the voltage source to decrease the duration of the time period during which a voltage is applied between the emitter and the counter-electrode at step (37). The time period is preferably decreased in a stepwise manner, in steps of 1 ms or less. Once the time period has been decreased and a voltage once more applied, the ammeter resumes measuring the current between the emitter and counter-electrode at step (33). Steps (33), (35) and (37) are repeated until a current is no longer measured or detected at step (35).

In between the time periods, the voltage is reduced to one that does not produce an electrospray, or is switched off, in other words reduced to a zero voltage. The voltage is preferably reduced in a manner that avoids the non-linear hysteresis effects associated with electrospraying. The switching off or reduction of the voltage to one that does not produce an electrospray denotes the start time and end time of a discrete time period. Once a current is no longer detected between the emitter and the counter-electrode at step (35), the processing module identifies and records the time period, having the shortest duration, for which a current was last detected in the system at step (39). This recorded time period, which corresponds to the shortest time period, is then used at step (41) to calculate the density of the fluid using the function:

$$T = 3^{\frac{3}{2}} \sqrt{\frac{\rho}{\varepsilon_0^3}} \left(\frac{\pi\gamma}{E^3}\right) \Rightarrow \rho = \left(\frac{\varepsilon_0}{3}\right)^3 \left(\frac{TE^3}{\pi\gamma}\right)^2,$$

wherein $\rho$ is the fluid density, $\varepsilon_0$ is the vacuum permittivity constant, T is the shortest time period, E is the electric field at an aperture of an emitter tip and $\gamma$ is the surface tension of the fluid.

In the embodiment described thus far the duration of the intermittent time periods during which the voltage is applied between the emitter and the counter-electrode is sequentially decreased in a step-wise manner. It will be appreciated by those skilled in the art that the time periods during which a voltage is applied need not necessarily decrease sequentially. It is merely required that at least some of the time periods during which a voltage is applied between the emitter and counter-electrode decrease in a progressive manner, in other words that at least some of the time periods become shorter in duration as the experiment progresses. It is therefore possible to have further time periods of increased or constant duration interspersed between those displaying a decreasing trend.

The method of determining a density of a fluid must essentially involve applying a voltage between the emitter and a counter-electrode spaced apart from the emitter for a number of intermittent time periods, wherein the duration of at least some, not necessarily all, of the time periods progressively decrease. Thus the shortest time period for which a current reading is obtained will be recorded and used to calculate the density of the fluid.

The duration of consecutive time periods may be varied in an alternating or even substantially random manner, wherein at least some of the time periods have a duration that progressively decreases. However, alternating the duration of the time periods between increasing and decreasing trends or having intermittent time periods of random duration is less desirable than having the duration of the time periods decrease in a sequential manner as it will result in a significant increase in the time it would take to execute the method, in other words the time to determine the density of a fluid will be increased.

It will also be appreciated that the duration of the progressively decreasing time periods, need not decrease in a linear manner, but could initially decrease in an exponential manner.

It may further be possible to implement a refinement of the duration of the time periods, in order to determine the shortest time period with higher resolution or a greater degree of accuracy. For example, if a current reading between two consecutive decreasing time periods is no longer obtained in the system, the time period may be increased slightly, in other words increased with a small increment in time to achieve a higher resolution, in which case you may once again obtain a current reading for current flowing between the emitter and the counter-electrode in the system. This current reading, which resulted from a small increase in the time period for applying the voltage may then be used as the "shortest" time period for the purpose of determining the density of the fluid. Alternatively, a further set of sequentially decreasing time periods at this higher resolution may be necessary to identify and record the shortest time period that can be used to determine the density of the fluid.

As is common with electrospraying apparatuses, the liquid is drawn through the chamber to the tip by the voltage (potential difference) that is applied between the tip and the counter-electrode. If required, a pump may also be included in the system to provide increased liquid flow rates.

Using software that is programmed onto a memory of the processing module, it is possible to operate the direct current voltage source, which may be adjustable, in such a manner that it applies a voltage that results in electrospray of the liquid for time periods of selected duration. Between each time period, the voltage is reduced to a voltage that does not result in an electrospray. The voltage source can be programmed to reduce the voltage to zero or to any voltage below the threshold voltage for electrospray in between each time period. The voltage source is also programmed to decrease the time periods in step-wise manner using pre-defined decrements until electrospraying stops and a net current is no longer detectable in the system. The decrements in the time period may be 1 ms or less and will depend on the configuration of the electrospray apparatus, the controllability of the voltage source, the experimental conditions, the voltage applied and the surface tension of the liquid, amongst other factors.

Current flows in the system if electrospraying occurs, i.e. if charged particles are making their way across the spacing between the tip of the emitter and the counter-electrode to complete the electrospraying circuit. As soon as current is absent in the system, following the application of a voltage for intermittent time periods having a decreasing duration, it implies that there was not sufficient time for a Taylor cone to form and for electrospray of the liquid to occur.

A Taylor cone, or electrospraying-cone jet, results when the rounded tip of the meniscus of the liquid present at the tip of the emitter deforms and expends a jet of particles. As the jet travels away from the tip, it becomes unstable and disintegrates into a plume of highly charged droplets. The droplets generated can have charge magnitudes close to the Rayleigh limit, which is the magnitude of charge required to overcome the surface tension force and promote droplet fission. The movement of the droplets from the tip of the emitter towards the counter-electrode forms a net ion current that completes the electrospraying circuit such that a net current is detected by the ammeter.

The time period for which (i) a voltage sufficient to produce an electrospray was applied in the system; (ii) a current reading was obtained; and (iii) which had the shortest possible duration, therefore, approximately corresponds to the time that is necessary for a Taylor cone of the liquid to form at the aperture of the emitter.

The time required for the Taylor cone to form was calculated in the past by Suvorov and Zubarev for liquid metals as:

$$T = 3^{\frac{3}{2}} \sqrt{\frac{\rho}{\varepsilon_0^3}} \left(\frac{\pi\gamma}{E^3}\right), \quad (1)$$

wherein T is the shortest time period, ρ is the liquid density, γ is the surface tension of the liquid, $\varepsilon_0$ is the vacuum permittivity constant and E is the electric field at an aperture of an emitter tip.

The above equation can be simplified by taking the following constant, $$\eta = \pi\left(3^{\frac{3}{2}}\right)\left(\sqrt{\varepsilon_0^{-3}}\right)$$

resulting in:

$$T = \eta\left(\frac{\gamma\sqrt{\rho}}{E^3}\right). \quad (2)$$

The time required to form a Taylor cone is also affected by the charge-relaxation time of the liquid, but generally this is several orders of magnitude smaller than the time it takes to form a Taylor cone. The charge-relaxation times are mostly in the range of between $10^{-10}$ and $10^{-5}$ seconds. The effects of dielectric polarization are taken into account.

Using equation (1) or (2), the density of a liquid can be determined if the time required to form a Taylor cone, the surface tension of the liquid, and the electric field at the tip of the emitter is known.

A selected density upper limit of $\rho_M$=2000 kg/m³ or more may be imposed to enable the allocation of sufficient time for the Taylor cone to form and electrospray to occur at the start of a density determination process. Consequently an upper limit time period, $T_M$, which is more than the time required to form a Taylor cone, $T_C$ will initially be used. The time period for the application of a voltage is then decreased, preferably sequentially in a step-wise manner by means of machine readable instructions on a processing module. As soon as current is no longer detected in the system, the processing module will issue machine readable instructions that the time period at which the last current reading was obtained be recorded, from which the density of the liquid, $\rho_C$, which will be less than $\rho_M$, is calculated using equation (1).

In order to calculate the density using equation (1), the surface tension of the liquid and the electric field at the aperture of the emitter tip must be known.

The surface tension of the liquid may be determined using the electrospray system of the current invention in the same experimental configuration in which it is for determining the density of the liquid. A method of determining the surface tension of a liquid using an electrospray system is outlined in the applicant's PCT International Publication Number WO 2015/128844 A1, which is by reference thereto, incorporated herein, in its entirety. Essentially, the surface tension and density of a liquid can be determined using the same electrospray system under the same experimental conditions.

The electric field at the aperture of the emitter tip can be calculated using the following equation:

$$E_{tip} = \frac{2V}{R\ln\left(\frac{4L}{R}\right)}, \quad (3)$$

wherein, V is the applied voltage, R is the emitter tip radius, and L is the electrode separation distance, i.e. the distance between the aperture of the emitter and the counter-electrode. The above equation does not take into account the effects of neither space charge nor polarization, which would result in a reduced field at the tip and is only valid for R<<L.

The critical voltage ($V_{crit}$) and electric field ($E_{crit}$) applied to the tip and the counter-electrode, initiating the liquid surface instability, and thus also the formation of a Taylor cone that leads to electrospraying, are given by the equations:

$$V_{crit} = \sqrt{\frac{\gamma R}{\varepsilon_0} \ln\left(\frac{4L}{R}\right)} \text{ and} \quad (4)$$

$$E_{crit} = 2\sqrt{\frac{\gamma}{\varepsilon_0 R}}.$$

When the Taylor cone is generated, a net ion current (I) is observed as the charged droplets are moving between the electrodes (assuming zero current contribution due to corona discharges or ion emissions):

$$I = \frac{f(\varepsilon)}{\sqrt{\varepsilon}} \sqrt{\gamma K Q}, \quad (5)$$

wherein $\varepsilon$ is the relative permittivity of the liquid, K is the electrical conductivity of the liquid, Q is the volumetric flow rate, and wherein the empirical function $f(\varepsilon)=\varepsilon/2$ is defined for $\varepsilon<40$ and $f(\varepsilon)=20$ for $\varepsilon\geq40$ respectively. The distance between the aperture of the emitter and the counter-electrode can be adjusted using, for example, a nanostepper motor.

The main effects that limit the capabilities of the system are electrical and corona discharges. The electrical fields generated by some electrospraying geometries are thus inhomogeneous, causing electric and, more specifically, corona discharge to occur before electrospraying. Corona discharge is an electrical discharge brought on by the ionization of fluid surrounding a conductor that is electrically energized. These types of discharges may occur when the strength of the electric field around a conductor is high enough to form a conductive region, but not high enough to cause electrical breakdown or arcing to nearby objects. Corona discharges are undesirable, as they result in sudden current increases that affect the Taylor cone stability, shorten the emitter lifetimes, particularly the capillary lifetimes and, most importantly, interfere with the determination of the time it takes to form a Taylor cone at the aperture of the emitter.

Consequently, the corona threshold electric field ($E_C$) must be considered, as it will determine the limitations of the method and system described, and can be determined according to the following equation:

$$E_C = \left(\frac{2\varepsilon+1}{2\varepsilon}\right)E_O, \text{ from } E_C = \left(\frac{b\varepsilon+1}{b\varepsilon}\right)E_O \text{ with } b=2, \quad (6)$$

where $\in$ is the relative permittivity of the liquid, and $E_0$ is the Rousse threshold. To obtain more accurate results, that are dependent on the aperture radius, the function $b(R)=p1 \cdot R+p2$, where $p1=11229$ m$^{-1}$ and $p2=0.1092$, should be employed. A relative permittivity of 5 may be selected to represent the majority of liquids.

The Rousse threshold electric field is given by equation (7):

$$E_O = 30 + 9R^{-0.5} \qquad R \geq 100 \text{ μm} \qquad (7)$$
$$= 62.7 + 1.74R^{-0.75} \quad 15 \text{ μm} < R < 100 \text{ μm}$$

where R is the radius of curvature of a rounded droplet with a hyperbolic point-to-plane geometry that has formed at the aperture of the electrospray system in centimeters. This equation returns a result in a kV/cm unit. It was verified by Cloupeau that equation 7 holds for radii of curvature as small as 2.5 μm. One can therefore determine, for a given liquid, the electric field at which undesirable corona discharge will occur.

Since the corona threshold electric field and the radius of the aperture of the electrospray system is known, the maximum surface tension ($\gamma_c$) of a liquid to be electrosprayed can be determined analytically, using equation 8:

$$\gamma_C = \frac{R\varepsilon_0}{4} E_C^2, \text{ suggesting } \gamma_C \sim R^{-0.5}, \qquad (8)$$

where R is the aperture tip radius, $\in_0$ is the relative permittivity of the atmosphere or the isolation medium, and $E_C$ is the corona threshold field.

In an embodiment of the invention the radius of the aperture in the emitter tip is selected to be 5 μm. If the radius of the aperture in the tip is selected to be 5 μm, the distance between the emitter tip and the counter-electrode should ideally be approximately ten times the radius, in other words 50 μm, in order to reduce the likelihood of electrical discharges occurring when relatively high voltages are applied. A separation distance-radius ratio of approximately 10:1 will result in the highest corona onset fields, enabling measurement of higher surface tension liquids without corona discharges obscuring the current reading. Using the selected distance of 50 μm, the density of the majority of liquids can be measured by applying a voltage of less than approximately 800 V. It is possible to use a separation distance-radius ratio of less than 10:1, but then a correction factor must be introduced in the model.

If necessary, the applied voltage may be maximized to measure high surface tension liquids by having a smaller aperture in the tip, such that a shorter distance between the tip and the counter-electrode is necessary and by using an isolation medium other than air such as, for example, an insulating and/or inert gas.

In one embodiment of the invention, borosilicate glass capillaries may be used as the emitter, which permits the temperature to be varied, using an external temperature controller that can heat or cool the emitter and thus the liquid that is being investigated. The system and method of the invention therefore also lends itself to conducting variable temperature density determination. The maximum temperature at which a determination can be done may be limited by the thermal properties of the material that the emitter or capillary is made of, in this embodiment the maximum temperature will be sufficiently high. The softening point of borosilicate glass, for example, is approximately 820° C. Borosilicate glass also has a low thermal expansion coefficient, which make it suitable for variable temperature measurements in an electrospraying apparatus.

Figure 3:
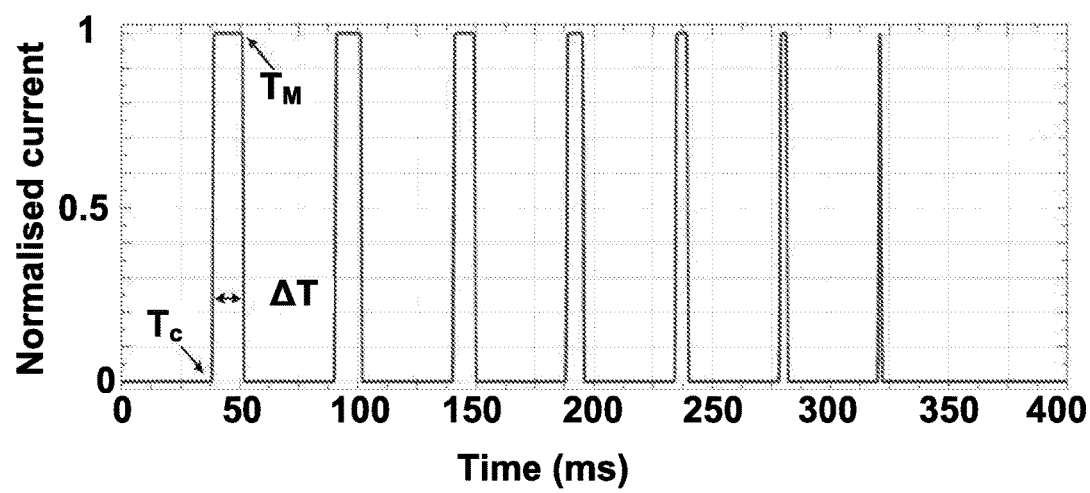
FIG. 3 is a simulation of the normalised current as a function of time whilst using an electrospray system to determine the density of ethylene glycol.

For exemplary purposes, simulated and normalized current measurements as a function of time using an electrospray system is shown in FIG. 3. The simulation demonstrates the use of an electrospray system to determine the density of ethylene glycol, with a surface tension of 45 mN/m and a known density of 1113 kg/m$^3$. An experimental configuration of a pulsed cone-jet electrospray system, as described by Kim et al. (Kim J., Oh H., Kim S. S., *Electrohydrodynamic drop-on-demand patterning in pulsed cone-jet mode at various frequencies*, Journal of Aerosol Science, 2008, 39, pp 819-825) is used for the simulation. The simulated current measurements shown in FIG. 3 are for an ideal system and background current from noise and interference signals likely to be present in reality, is not shown.

Using the density upper limit, $\rho_M$, a formation time upper limit, $T_M$=51 ms, is calculated, whilst the actual formation time is $T_C$=38.14 ms. From FIG. 3, it is apparent that the current is zero until a Taylor cone forms after approximately 38 ms. A current is measured until the formation time upper limit $T_M$ of 51 ms is reached, after which the current drops to zero. If the time period for applying the voltage, is incrementally decreased, the time during which electrospray occurs and during which current is detected, $\Delta T$, decreases. If the time period for applying the voltage is decreased so as to not allow sufficient time for the Taylor cone to form, a current will no longer be read by the ammeter. The time period corresponding to the last current reading, when the time period for applying the voltage is approximately equal to $T_C$ (38.14 ms), is recorded and is regarded as the actual time required to form a Taylor cone, which is then used to calculate the density, $\rho_C$, of the liquid by solving a rearranged version of equation (1) in the following manner:

$$\rho = \left(\frac{\varepsilon_0}{3}\right)^3 \left(\frac{TE^3}{\pi\gamma}\right)^2$$
$$= \left(\frac{8.854187817 \times 10^{-12} \frac{F}{m}}{3}\right)^3 \left(\frac{38.14 \text{ ms} \times \left(2.9 \times 10^6 \frac{V}{m}\right)^3}{\pi\left(4.5 \times 10^{-2} \frac{N}{m}\right)}\right)^2$$
$$= 1113 \text{ kg/m}^3.$$

In the above-described example, it is assumed that the surface tension of the liquid is known. In the case that the method and system according to the invention is to be used to determine the density of an unidentified liquid or mixture of liquids, it is possible to use the electrospray system, as described herein and according to the method and system described in the applicant's PCT International Publication Number WO 2015/128844 A1, to also determine the surface tension of the unknown liquid or mixture of liquids prior to determining liquid density.

The accuracy of the proposed system will primarily depend on the size of the decrements in which the time period for applying a voltage is decreased as well as the sensitivity of the device that measures current. The accuracy will also depend on the synchronization quality between the devices for measuring the voltage and current, the voltage source, and the processing module, amongst other factors.

Unlike known methods of determining the density of liquids, the system and method described herein uses an amount of liquid in the micro-liter range per density determination owing to the low flow rates of the liquid towards the tip and the small aperture size. The liquid is not under hydrostatic pressure, but is drawn out of the emitter by the applied voltage. The sample volume for a single density determination is a fraction of that used by most known methods for the determination of liquid density. Furthermore, the system and method described herein provides the possibility of very short measurement times per sample and high accuracy for density determinations.

The above description is by way of example only and it should be appreciated that numerous changes and modifications may be made to the system and method described, without departing from the scope of the invention. It should, for example, be immediately apparent that if the voltage source is capable of being digitally controlled by specifying the exact voltage it is to apply, then the need for an additional device for measuring the voltage, such as a voltmeter, in the system may be alleviated, as the exact voltage applied between the emitter and counter-electrode will already be known. The voltmeter does, however, act as a control mechanism to provide feedback with regard to whether a voltage is successfully applied and in the manner it was programmed to be applied. It will be apparent to those skilled in the art that any suitable device(s) can be used to measure voltage and/or current.

Moreover, it will be appreciated by one skilled in the art that the method and system for determining the density of a fluid may be used for fluids, which includes liquids or relatively dense gases with fluid-like properties.

It will also be apparent to those skilled in the art that the operation of the system may be controlled by suitable software instructions and algorithms and that the calculations used to derive the density of a liquid from the shortest time period may be programmed onto the processing module. The system of the invention may therefore be provided as a standalone unit, or may be connectable to existing, external processors or other computers.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A method of determining a density of a fluid, the method including the steps of:
   introducing the fluid into an emitter of an electrospraying apparatus;
   applying a voltage between the emitter and a counter-electrode spaced apart from the emitter for a number of intermittent time periods, wherein the duration of at least some of the time periods during which the voltage is applied progressively decreases;
   measuring current between the emitter and the counter-electrode for each time period;
   identifying and recording a shortest time period for which a current reading between the emitter and counter-electrode is obtained; and
   calculating the density of the fluid as a function of the shortest time period.

2. The method as claimed in claim 1, wherein the density of the fluid is calculated using the function:

$$\rho = \left(\frac{\varepsilon_0}{3}\right)^3 \left(\frac{TE^3}{\pi\gamma}\right)^2,$$

wherein $\rho$ is the fluid density, $\varepsilon_0$ is the vacuum permittivity constant, T is the shortest time period, E is the electric field at an aperture of an emitter tip, and $\gamma$ is the surface tension of the fluid.

3. The method as claimed in claim 1, wherein the voltage applied between the emitter and the counter-electrode during time periods is sufficient to produce an electrospray of the fluid and wherein the voltage is reduced to a voltage that does not produce an electrospray of the fluid, or is switched off, in between the time periods.

4. The method as claimed in claim 1, wherein the time periods during which the voltage is applied start with an initial time period that is associated with a selected upper density limit so as to allocate sufficient time for electrospraying to occur.

5. The method as claimed in claim 1, wherein the duration of the time periods during which the voltage is applied decreases sequentially in a step-wise manner.

6. The method as claimed in claim 5, wherein the duration of the time periods during which the voltage is applied decreases in steps of 1 ms or less.

7. The method as claimed in claim 4, wherein the initial time period is associated with an upper density limit that is more than or equal to 2000 kg/m$^3$.

8. A system for measuring a density of a fluid comprising an electro spraying apparatus having an emitter through which the fluid is drawn,
   at least one counter-electrode spaced apart from the emitter, and
   a voltage source configured to apply a voltage between the emitter and the counter-electrode to create an electrospray of the fluid from the emitter,
   a device for measuring the voltage applied between the emitter and the counter-electrode and
   a device for measuring the current flowing in the system as a result of electrospray of the fluid between the emitter and the counter-electrode and for measuring the current between the emitter and the counter-electrode for each time period;
   wherein
   a processing module in communication with at least the voltage source, the voltage measuring device and the current measuring device, is configured to operate the voltage source to apply a voltage between the emitter and the counter electrode for a number of intermittent time periods,
   wherein the duration of at least some of the time periods during which the voltage is applied is progressively decreased, and
   wherein the processing module is further configured to read the current measuring device, and to record the shortest time period for which a current reading between the emitter and the counter-electrode is obtained in the system; and
   wherein the processor module or an external processor connectable to the processing module is configured to calculate the density of the fluid as a function of the shortest time period.

9. The system as claimed in claim 8, wherein the processing module is configured to calculate the density of the fluid as a function of the shortest time period.

10. The system as claimed in claim 9, wherein the function is:

$$\rho = \left(\frac{\varepsilon_0}{3}\right)^3 \left(\frac{TE^3}{\pi\gamma}\right)^2,$$

wherein ρ is the fluid density, $\varepsilon_0$ is the vacuum permittivity constant, T is the shortest time period, E is the electric field at an aperture of an emitter tip and γ is the surface tension of the fluid.

11. The system as claimed in claim 8, wherein the voltage source is a programmable direct current voltage source.

12. The system as claimed in claim 8, wherein a software application is resident on the processing module and executable by the processing module to progressively decrease at least some of the time periods for which a voltage is applied.

13. The system as claimed in claim 12, wherein a software application is resident on the processing module and executable by the processing module to sequentially decrease the time periods in a step-wise manner, to stop decreasing the time period when a current is no longer detected by the current measuring device and to reduce the voltage to a voltage that does not produce an electrospray, or switch the voltage off, in between the time periods.

14. The system as claimed in claim 8 wherein the electrospray apparatus is configured to electrospray in air and under atmospheric conditions.

15. The system as claimed in claim 8, wherein the electrospray apparatus is configured to electrospray within an insulating gas and wherein at least the electrospray apparatus and the counter-electrode are located within a hermetically sealed container filled with the insulating gas.

* * * * *